United States Patent [19]

Nakaseko et al.

[11] Patent Number: 5,665,680
[45] Date of Patent: Sep. 9, 1997

[54] METHOD FOR INCREASING YIELD OF SOYBEAN BY INHIBITION OF GIBBERELLIN BIOSYNTHESIS

[75] Inventors: Kimio Nakaseko, Sapporo; Hideyuki Shibata, Kobe; Seigo Ouchi, Toyonaka; Akira Nishikawa, Akashi, all of Japan

[73] Assignee: Sumitomo Chemical Company, Limited, Osaka, Japan

[21] Appl. No.: 515,246

[22] Filed: Aug. 16, 1995

[30] Foreign Application Priority Data

Aug. 24, 1994 [JP] Japan ................... 6-199384

[51] Int. Cl.⁶ .................. A01N 43/653; A01N 43/40; A01N 35/06; A01N 43/54
[52] U.S. Cl. .................. 504/239; 504/244; 504/262; 504/320
[58] Field of Search .................. 504/262, 244, 504/320, 239

[56] References Cited

U.S. PATENT DOCUMENTS

| | | | |
|---|---|---|---|
| 4,002,628 | 1/1977 | Benefiel et al. | 260/251 |
| 4,554,007 | 11/1985 | Funaki et al. | 71/76 |
| 5,006,154 | 4/1991 | Kaplan et al. | 71/92 |
| 5,298,482 | 3/1994 | Tanaka et al. | 504/320 |
| 5,532,206 | 7/1996 | Evans et al. | 504/176 |

FOREIGN PATENT DOCUMENTS

| | | |
|---|---|---|
| 1088075 | 10/1980 | Canada . |
| 53-28170 | 3/1978 | Japan . |
| 55-111477 | 8/1980 | Japan . |
| 56-25105 | 3/1981 | Japan . |
| 61-87642 | 5/1986 | Japan . |
| 64-52691 | 2/1989 | Japan . |
| 2-154624 | 6/1990 | Japan . |
| 1218623 | 1/1971 | United Kingdom . |

OTHER PUBLICATIONS

The Pesticide Manual, Tenth Edition, Crop Protection Publications (1994), pp. 1031–1035, 41–42, 507–508, 765–766, and 838.

Short Review of Herbicides PGRS, pp. 306 and 316. Hodogaya Chem. Co. 1990.

Complete Book of Field Farming Fundamental Physiology and Applied Technology (1981), pp. 83–84. (Japanese).

Rademacher et al. "Tetracyclis and Triazole–type Plant Growth Retardants: Their Influence on the Biosynthesis of Gibberellins and Other Metabolic Processes". *Pesticide Science*. 21:241–252. 1987.

Izumi et al. "Studies of Sites of Action of a New Plant Growth Retardant . . . (S–3307) and Comparative Effects of Its Stereoisomers . . . " *Plant Cell Physiology*. 26(5):821–827. 1985.

Hedden et al. "Inhibition of Gibberellin biosynthesis by Paclobutrazol in Cell–free Homogenates . . . " *J. Of Plant Growth Regulation*. 4:111–122. 1985.

*Primary Examiner*—S. Mark Clardy
*Attorney, Agent, or Firm*—Sughrue, Mion, Zinn, Macpeak & Seas

[57] ABSTRACT

Provided is a method for increasing yield of soybean by foliar application of a gibberellin biosynthesis inhibiting type compound to soybean plants at the time of formation of pollen, at the time of formation of embryo sac or at the time of flowering.

14 Claims, No Drawings

METHOD FOR INCREASING YIELD OF SOYBEAN BY INHIBITION OF GIBBERELLIN BIOSYNTHESIS

FIELD OF THE INVENTION

The present invention relates to a method for increasing yield of soybean and a yield increasing agent.

DESCRIPTION OF THE RELATED ART

As methods for increasing yield of soybean, a method of applying fertilizers such as nitrogen, phosphate and potassium and selection of superior plant species capable of giving high yield according to a breeding method are generally known.

However, in the case of increasing the yield by application of fertilizers, a proper control of the fertilizers suitable for the cultivation soil is essential for exhibiting the effect at maximum, and sometimes, excessive application of fertilizers results in lodging of plants to cause decrease in the crop. In the case of selecting superior plant species by the breeding method, a long time of years and much labor are required, and in addition, there are the problems that a great increase of yield cannot necessarily be expected and even if superior plants can be bred, they differ in adaptability to areas of cultivation and they cannot be utilized with ease in a wide variety of areas.

As a result of intensive research conducted by the inventors, it has been found that yield of soybean can be markedly and easily increased irrespective of cultivation areas by foliar application of a specific compound to soybean plants in a specific stage. Thus, the present invention has been accomplished.

SUMMARY OF THE INVENTION

That is, the present invention provides a method for increasing yield of soybean, comprising foliar application of a compound having gibberellin biosynthesis inhibiting activity to soybean plants at any time of formation of pollen or formation of embryo sac or at the time of flowering (hereinafter referred to as "method of the present invention"), and it further provides a yield increasing agent.

DESCRIPTION OF THE PREFERRED EMBODIMENTS

The plants to which the present invention is applied are soybean plants which belong to the genus Glycine max (Glycine max Merr.). As the soybean plants, mention may be made of, for example, var. Enrei, Tamahomare, Kitamishiro, Toyosuzu, Kitamusume, Kitahomare, Toyomusume, Kariyutaka, Koganejiro, Tsurukogane, Suzuhime, Miyagishirome, Okuhara HS No. 1, Sloan, Davis, Foscalin, etc.

The compounds to be used in the present invention have gibberellin biosynthesis inhibiting activity.

The gibberellin biosynthesis inhibiting type compounds are, for example, those which have typical actions such as inhibition of growth. Representative examples of the compounds are triazole compounds such as (E)-1-(4-chlorophenyl)-4,4-dimethyl-2-(1,2,4-triazol-1-yl)-1-penten-3-ol (described in Japanese Patent Kokai No.56-25105) or salts thereof, (2RS, 3RS)-1-(4-chlorophenyl)-4,4-dimethyl-2-(1H-1,2,4-triazol-1-yl)pentan-3-ol (described in Japanese Patent Kokai No.53-28170) or salts thereof, (E)-1-cyclohexyl-4, 4-dimethyl-2-(1H-1,2,4-triazol-1-yl)-1-penten-3-ol (described in Japanese Patent Kokai No.55-111477) or salts thereof, and rel=(1R, 2R, 6S, 7R, 8R, 11S)-5-(4-chlorophenyl)-3, 4,5,9,10-penta-azatetracyclo-[5.4.1.0$^{2,6}$.0$^{8,11}$]=dodeca-3, 9-diene (described in "Short Review of Herbicides & PGRs", page 316, (1990) published from Hodogaya Chemical Co., Ltd.); isonicotinanilide compounds such as 4'-chloro-2'-(α-hydroxybenzyl) isonicotinanilide (described in "Short Review of Herbicides & PGRs", page 306, (1990) published from Hodogaya Chemical Co., Ltd.); 3,5-dioxo-4-propionylcyclohexanecarboxylic acid calcium salt and pyrimidine compounds such as (RS)-2-methyl-1-pyrimidin-5-yl-1-(4-trifluoromethoxyphenyl) propan-1-ol (described in U.S. Pat. No. 4002628 or "The Pesticidal Manual", Tenth Edition, page 507) and α-cyclopropyl-4-methoxy-α-(pyrimidin-5-yl)benzyl alcohol (described in U.S. Pat. No. 1218623 or "The Pesticidal Manual", Tenth Edition, page 41). These compounds may be used each alone or in admixture of two or more. If they have optical active isomers, there may be used the optical active isomers having gibberellin biosynthesis inhibiting activity.

These gibberellin biosynthesis inhibiting type compounds are usually formulated into emulsifiable concentrates, liquids, wettable powders, suspension formulations, granules and the like using a solid or liquid carrier, a surfactant and other auxiliaries for formulation. These formulations contain the active ingredient in an amount of normally about 0.00001 to about 99.9% by weight.

The liquid carriers include, for example, aromatic hydrocarbons such as xylene and methylnaphthalene, alcohols such as isopropanol, ethylene glycol and cellosolve, ketones such as acetone, cyclohexanone and isophorone, vegetable oils such as soybean oil and cotton seed oil, dimethyl sulfoxide, acetonitrile, water and the like.

The solid carriers include, for example, fine powders or granules of kaolin clay, attapulgite clay, bentonite, acid clay, pyrophyllite, talc, diatomaceous earth, calcite, walnut shell powder, urea, ammonium sulfate, synthetic hydrated silicon oxide and the like.

As the surfactants used for emulsification, dispersion, wetting, spreading, bonding, disintegration controlling, stabilization of active ingredients, improvement of fluidity and rust prevention, any of nonionic, anionic, cationic and amphoteric surfactant may be used, but ordinarily nonionic and/or anionic ones are used. Representative examples of the nonionic surfactant are polyoxyethylene alkyl ethers, polyoxyethylene alkylaryl ethers, polyoxyethylene polyoxypropylene block copolymers, sorbitan fatty acid esters and polyoxyethylene sorbitan fatty acid esters. Representative examples of anionic surface active agents are salts of alkylsulfate esters, alkyl(aryl)sulfonates, dialkylsulfosuccinates, and salts of polyoxyethylene alkylaryl ether phosphoric acid esters.

The other auxiliaries for formulation include, for example, lignosulfonates, alginates, polyvinyl alcohol, gum arabic, CMC (carboxymethyl cellulose), PAP (acid isopropyl phosphate) and the like.

Concentration and dosage of thus formulated gibberellin biosynthesis inhibiting type compounds vary depending on the kind of the compounds and usually, a solution containing about 0.01 to about 1000 ppm of the active ingredient is applied at a rate of about 0.1 to about 50000 g/ha in terms of amount of the active ingredient, preferably about 0.1 to about 5000 g/ha in the case of the triazole compounds and preferably about 1 to about 50000 g/ha in the case of the isonicotinanilide compounds. As far as the effect of the present invention is not damaged, the gibberellin biosynthesis inhibiting type compound may be used in admixture with fertilizers, insecticides, fungicides, herbicides and plant growth regulators.

The timing of application of the compound, namely, "the time of pollen formation, the time of embryo sac formation or the time of flowering" will be explained.

In the present invention, it is essential to foliar-spray the compound to soybean plants at any stage of pollen formation, the stage of embryo sac formation or the stage of flowering. Preferred application time is in the period of pollen formation or embryo sac formation or in the period of one week from starting of flowering, and especially preferred is the period of one week from starting of flowering.

The flower of soybean is made through the stages of formation of bract, sepal, stamen, pistil, ovule, pollen and embryo sac, and generally it takes about 25–30 days in total though it depends on weather, cultivars, cultivating conditions, etc. ("Series of Dry Field Farming (Beans)— Basic Physiology and Applied Technique—", pages 83–84, edited by Nobunkyo, published from Nosangyoson Bunka Kyokai on Aug. 15, 1981). In these stages, period of formation of stamen corresponds to about 15 days to about 20 days prior to flowering, that of formation of pistil corresponds to about 10 days to about 15 days prior to flowering, that of formation of ovule corresponds to about 7 days to about 15 days prior to flowering, that of formation of pollen corresponds to about 3 days to about 7 days prior to flowering and that of formation of embryo sac corresponds to about 1 day to about 7 days prior to flowering. Therefore, the period of formation of pollen and that of formation of embryo sac in the present invention correspond to the final stage in the course of formation of flowers of soybean plants and, for example, this stage is a period of about 1 day to about 7 days prior to flowering. However, such days prior to flowering may vary depending on weather, cultivars, cultivating conditions, etc.

On the other hand, the period of flowering may be as long as 6 weeks depending on weather, cultivars, cultivating conditions, etc., but usually about 3 weeks to about 4 weeks.

The method of application of the compound is foliar application by spraying, dusting, etc.

The present invention will be explained in detail by the following nonlimiting formulation examples and test examples.

First, the formulation examples will be shown, in which parts are by weight.

Formulation Example 1 (Emulsifiable concentrate)

Xylene was added to 5 parts of (E)-1-(4-chlorophenyl)-4,4-dimethyl-2-(1,2,4-triazol-1-yl)-1-pen ten-3-ol (hereinafter referred to as "compound A"), 10 parts of polyoryethylene styrylphenyl ether and 50 parts of cyclohexanone to make up 100 parts in total, followed by stirring and mixing to obtain an emulsifiable concentrate.

Formulation Example 2 (Wettable powder)

Kaolin clay was added to 10 parts of (2RS, 3RS)-1-(4-chlorophenyl)-4,4-dimethyl-2-(1H-1,2,4-triazo 1-1-yl) pentan-3-ol (hereinafter referred to as "compound B"), 5 parts of sodium laurylsulfate and 2 parts of aromatic sulfonate/formalin condensate to make up 100 parts in total, followed by well mixing them by a juice mixer and then pulverizing by a jet mill to obtain a wettable powder.

The test examples will be shown below.

Test Example 1

Soybean (var. Enrei) was sowed in soil filled in a pot (17 cm in diameter and 15 cm in height) and cultivated in a glass greenhouse. A 3 ppm solution of the compound A formulated into an emulsifiable concentrate in accordance with Formulation Example 1 was foliar-sprayed to the plant on the day of starting of flowering (46 days after sowing) at a dosage of 1000. L/ha. After cultivation for 112 days from sowing, the yield was examined. The yield is shown by the grain yield which is the product of the total number of grains per one plant and the average weight of one grain. The number of the total grains means the number of ripening ovules which is the difference between the total number of ovules and the number of ovules having undeveloped grains which did not develop as fruits in the course of growing. Actually, the yield was obtained by screening the ripening ovalues from grains which did not grow as fruits by pressing through a 5.66 mm-mesh screen.

The results are shown in Table 1. The test was replicated 5 times for one group. The yield was the average value of the results obtained by replication of 5 times and shown by a relative value assuming the yield of control group (untreated group) to be 100%.

As is clear from Table 1, the group of the present invention showed remarkably high yield increasing effect as compared with the control group (untreated group).

TABLE 1

|  | The group of the present invention | Control group |
| --- | --- | --- |
| Concentration of treating solution (ppm) | 3 | 0 |
| Yield (%) | 184.7 | 100.0 |

Test Example 2

A test was conducted in the same manner as in Test Example 1, except that the concentration of the compound A in the solution was 10 ppm instead of 3 ppm. The results are shown in Table 2.

As is clear from Table 2, the group of the present invention showed remarkably high yield increasing effect as compared with the control group (untreated group) as in the Test Example 1.

TABLE 2

|  | The group of the present invention | Control group |
| --- | --- | --- |
| Concentration of treating solution (ppm) | 10 | 0 |
| Yield (%) | 182.3 | 100.0 |

Test Example 3

A test was conducted in the same manner as in Test Example 1, except that compound B in treating concentration (ppm): 100 instead of compound A in treating concentration (ppm): 3. As a result, the similar yield increasing effect to that in Test Example 1 was obtained.

Test Example 4

Soybean (var. Enrei) was sowed in soil filled in a pot (17 cm in diameter and 15 cm in height) and cultivated in a glass greenhouse. A 10 ppm solution of the compound A formulated into an emulsifiable concentrate in accordance with Formulation Example 1 was foliar-sprayed to the plant at a dosage of 1000 L/ha on the 9th day prior to flowering which was in the period of formation of ovule (the 37th day after sowing: comparative group 1), on the day of starting of flowering (the 46th day after sowing: the group of the present invention), and on the day following completion of flowering (the 65th day after sowing: comparative group 2). After cultivation for 112 days from sowing, the yield was examined in the same manner as in Test Example 1. The results are shown in Table 3. The test was replicated 5 times for one group. The yield was the average value of the results obtained by repetition of 5 times and shown by a relative value assuming the yield of control group (untreated group) to be 100%.

As is clear from Table 3, the group of the present invention showed remarkably high yield increasing effect as compared with the comparative group and the control group.

TABLE 3

|  | Group of the present invention | Comparative group 1 | Comparative group 2 | Control group |
| --- | --- | --- | --- | --- |
| Concentration of treating solution (ppm) | 10 | 10 | 10 | 0 |
| Yield (%) | 182.3 | 115.7 | 118.1 | 100.0 |

Test Example 5

Soybean (var. Okyhara HS No. 1) was sowed in soil filled in a pot (17 cm in diameter and 15 cm in height) and cultivated in the open air. The compound A, the compound B, 4'-chloro-2'-(α-hydroxybenzyl)-isonicotinanilide (hereinafter referred to as "compound C"), α-cyclopropyl-4-methoxy-α-(pyrimidin-5-yl) benzyl alcohol (hereinafter referred to as "compound D") and 3,5-dioxo-4-propionylcyclohexanecarboxylic acid calcium salt (hereinafter referred to as "compound E") were formulated into wettable powder in accordance with Formulation Example 2.

A 10 ppm solution of the compound A, a 100 ppm solution of the compound B, a 2000 ppm solution of the compound C, a 100 ppm solution of the compound D and a 25 ppm solution of the compound E were foliar-sprayed to the plant on the day of flowering (51 days after sowing) at a dosage of 500 L/ha. After cultivation for 86 days from sowing, the yield was examined in the same manner as in Test Example 1. The results are shown in Table 4.

The test was replicated 7 times for one group. The yield was the average value of the results obtained by repetition of 7 times and shown by a relative value assuming the yield of control group (untreated group) to be 100%.

As is clear from Table 4, the groups of the present invention showed remarkably high yield increasing effect as compared with the control group (untreated group).

TABLE 4

|  | Compound | Concentration of treating solution (ppm) | Yield (%) |
| --- | --- | --- | --- |
| Groups of the present invention | A | 10 | 120.0 |
|  | B | 100 | 120.8 |
|  | C | 2000 | 136.6 |
|  | D | 100 | 133.7 |
|  | E | 25 | 126.7 |
| Control group |  | 0 | 100.0 |

According to the present invention, it has become possible to markedly and easily increase the yield of soybean irrespective of areas of cultivation.

What is claimed is:

1. A method for increasing yield of soybean, which comprises foliar-applying an effective amount of a compound having a gibberellin biosynthesis inhibiting activity to soybean plants at the time of formation of pollen, at the time of formation of embryo sac or at the time of flowering.

2. A method according to claim 1, wherein the compound having a gibberellin boisynthesis inhibiting activity is a triazole compound, an isonicotinanilide compound or a pyrimidine compound.

3. A method according to claim 1, wherein the compound having a gibberellin biosynthesis inhibiting activity selected froma group consisting of (E)-1-4-chlorophenyl)-4,4-dimethyl-2-(1,2,4-triazol-1-yl)-1-penten-3-ol or a salt thereof or (2RS, 3RS)-1-(4-chlorophenyl)-4,4-dimethyl-2-(1H-1,2,4-triazol-1-yl)-pentan 3-ol or a salt thereof, 3,5dioxo-4-propionylcyclohexanecarboxylic acid calcium salt, and 4'-cjloro-2'-(α-hydroxybenzyl)isonicotinanilde or a salt thereof.

4. A method for increasing yield of soybean, which comprises foliar-applying an effective amount of (E)-1-(4-chlorophenyl)-4,4-dimethyl -2-(1,2,4-triazol-1-yl)-1-penten-3-ol or a salt thereof to soybean plants at the time of formation of pollen, at the time of formation of embryo sac or at the time of flowering.

5. A method according to claim 1, wherein the compound application is at pollen formation.

6. A method according to claim 1, wherein the compound application is at flowering.

7. A method according to claim 2, wherein the applied compound is a triazole compound.

8. A method according to claim 2, wherein the applied compound is an isonincotinanilide compound.

9. A method according to claim 2, wherein the applied compound is a pyrimidine compound.

10. A method according to claim 3, wherein the applied compound is (E)-1-(4-chlorophenyl)-4,4-dimethyl-2-(1,2,4-triazol-1-yl)-1-penten-3-ol.

11. A method according to claim 3, wherein the applied compound is (2RS, 3RS)-1-(4-chlorophenyl)-4,4-dimethyl-2-(1H-1,2, 4-triazol-1-yl)-pentan-3-ol.

12. A method according to claim 3, wherein the applied compound is 3,5-dioxo-4-propionylcyclohexanecarboxylic acid calcium salt.

13. A method according to claim 3, wherein the applied compound is 4'-chloro-2'-(alpha-hydroxybenzyl) isonicotinanilide.

14. A method according to claim 1 wherein the compound application is at embryo sac formation.

* * * * *